(12) United States Patent
Chen et al.

(10) Patent No.: US 7,195,647 B2
(45) Date of Patent: Mar. 27, 2007

(54) ARTIFICIAL KNEE JOINT

(76) Inventors: Chien-Liang Chen, 7F, No. 136, Sec. 2, Ho-Ping W. Rd., Taipei City (TW); Chien-Chuan Chen, 7F, No. 136, Sec. 2, Ho-Ping W. Rd., Taipei City (TW); I-Chun Chen, 7F, No. 136, Sec. 2, Ho-Ping W. Rd., Taipei City (TW)

( * ) Notice: Subject to any disclaimer, the term of this patent is extended or adjusted under 35 U.S.C. 154(b) by 589 days.

(21) Appl. No.: 10/745,564

(22) Filed: Dec. 29, 2003

(65) Prior Publication Data

US 2005/0143839 A1 Jun. 30, 2005

(51) Int. Cl.
*A61F 2/64* (2006.01)

(52) U.S. Cl. .................................................. 623/45

(58) Field of Classification Search ............. 623/39–46
See application file for complete search history.

(56) References Cited

U.S. PATENT DOCUMENTS 6,355,071 B1 * 3/2002 Cheng ......................... 623/45

FOREIGN PATENT DOCUMENTS

WO    WO 01/43668 A1 *  6/2001

* cited by examiner

*Primary Examiner*—David H. Willse
(74) *Attorney, Agent, or Firm*—Foley & Lardner LLP (57) ABSTRACT

An artificial knee joint includes an upper seat, a lower seat adapted to be connected fixedly to a prosthetic lower leg, and a driving device. The upper seat includes a seat body connected to the lower seat by the driving device, and a movable member connected pivotally to the seat body and adapted to be connected fixedly to a residual thigh. The driving device includes a rotating shaft journalled within the seat body. When a downward force and an upward force are applied respectively to the movable member and the seat body, a gripping member presses against the rotating shaft so as to prevent rotation of the rotating shaft and thus relative movement of the lower seat and the seat body of the upper seat.

4 Claims, 8 Drawing Sheets

ARTIFICIAL KNEE JOINT

BACKGROUND OF THE INVENTION

1. Field of the Invention

This invention relates to an artificial knee joint, and more particularly to an artificial knee joint that includes a gripping member, which is movable to press against a rotating shaft so as to prevent relative rotation of a residual thigh of a prosthesis wearer and a prosthetic lower leg.

2. Description of the Related Art

Figure 1:
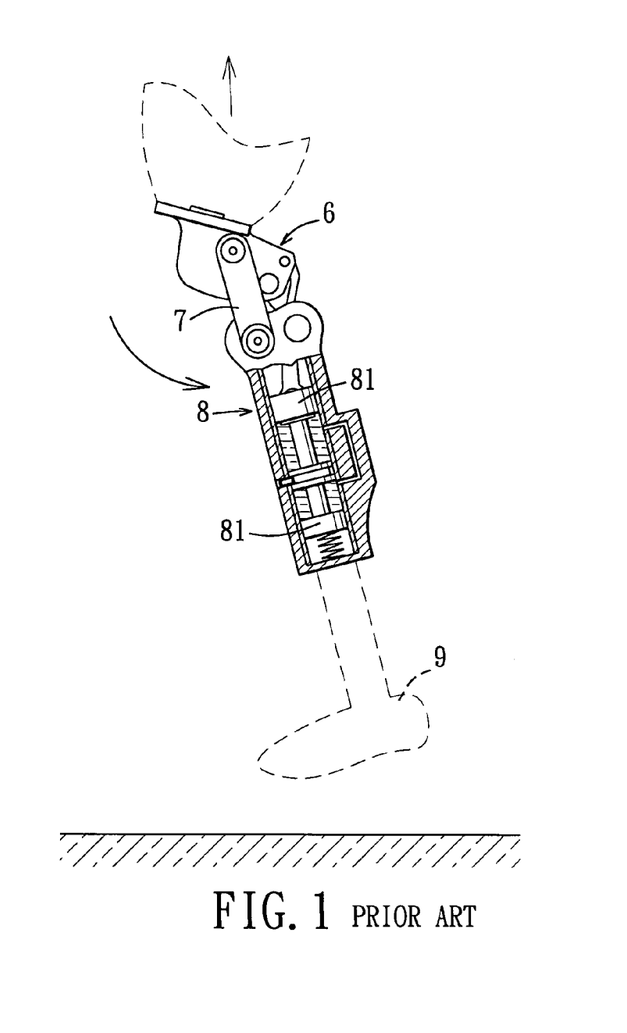
FIG. 1 is a schematic sectional view of a conventional artificial knee joint, illustrating how a prosthetic lower leg is inclined relative to a residual thigh of a prosthesis wearer when the residual thigh is raised.
Figure 2:
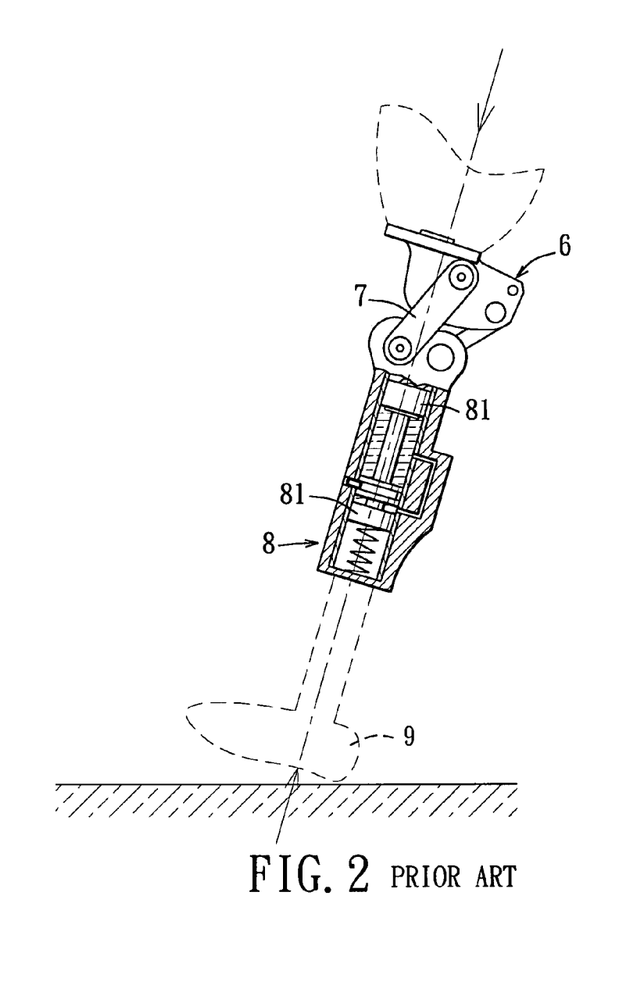
FIG. 2 is a schematic sectional view of the conventional artificial knee joint, illustrating how the prosthetic lower leg is aligned with the residual thigh when the prosthetic lower leg is pressed against the ground by the residual thigh.

Referring to FIGS. 1 and 2, a conventional artificial knee joint is shown to include an upper seat 6 adapted to be connected fixedly to a residual thigh (not shown) of a prosthesis wearer, a driving device 7, and a lower seat 8 connected to the upper seat 6 by the driving device 7 and adapted to be connected fixedly to a prosthetic lower leg 9. The lower seat 8 is configured as a hydraulic cylinder, and is provided with two pistons 81 so as to retard relative movement of the upper and lower seats 6, 8.

When the prosthesis wearer walks on a planar ground surface, the residual thigh can be raised to separate the prosthetic lower leg 9 from the planar ground surface such that the prosthetic lower leg 9 is inclined relative to the residual thigh, as shown in FIG. 1. Subsequently, the residual thigh is moved frontwardly and downwardly to permit the prosthetic lower leg 9 to contact the planar ground surface such that the prosthetic lower leg 9 is aligned with the residual thigh. As such, the prosthetic lower leg 9 can support the residual thigh on the planar ground surface.

Figure 3:
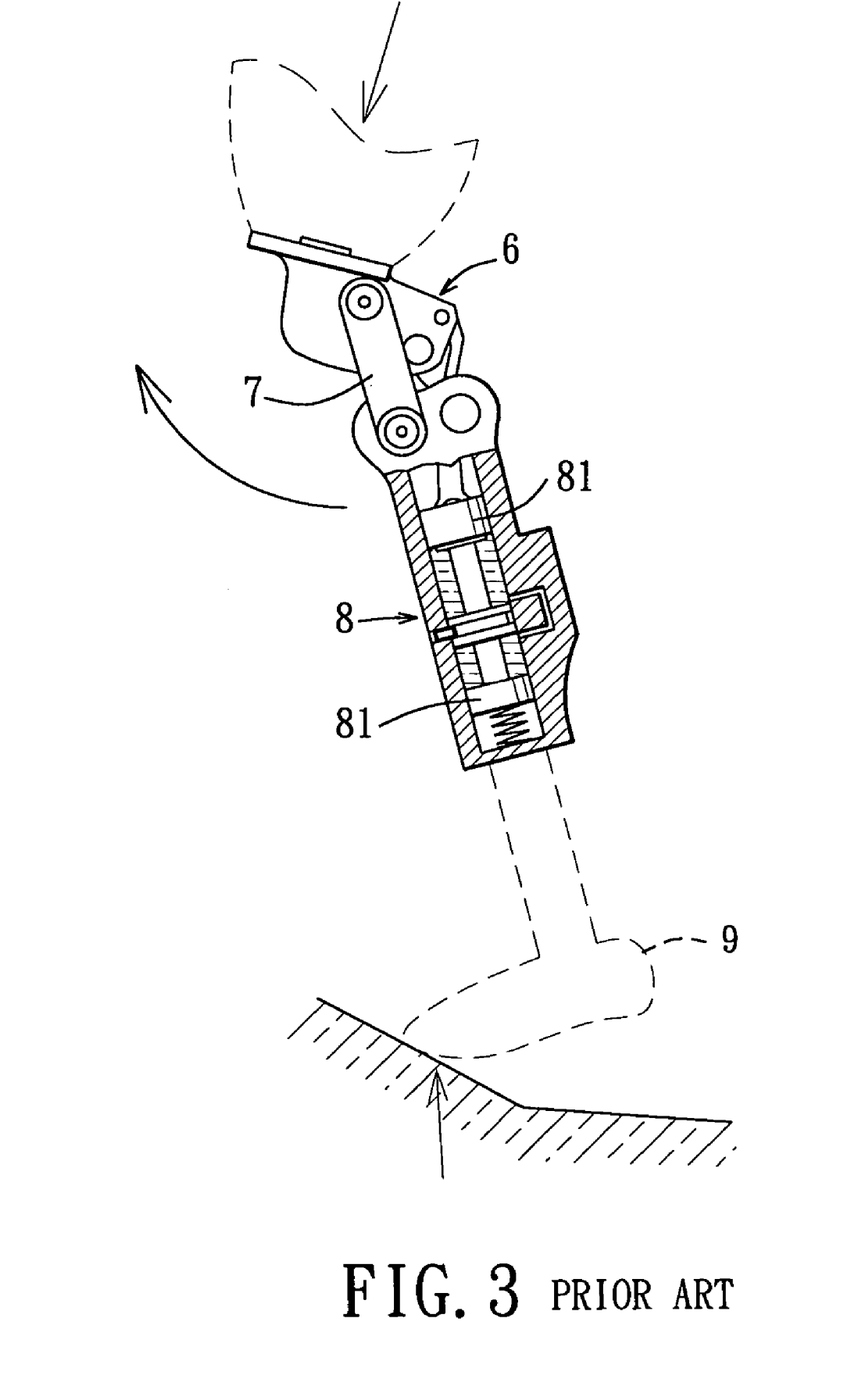
FIG. 3 is a schematic sectional view of the conventional artificial knee joint, illustrating how the prosthetic lower leg cannot be aligned with the residual thigh when the prosthesis wearer walks on an inclined ground surface.

Referring to FIG. 3, when the prosthesis wearer walks on an inclined ground surface, it is difficult to raise the residual thigh to a sufficient height to permit the prosthetic lower leg 9 to align with the residual thigh when the prosthetic lower leg 9 is moved downwardly to contact the inclined ground surface. As such, the prosthesis wearer may fall down due to the fact that a downward force and an upward force are applied respectively to the residual thigh and the prosthetic lower leg 9.

SUMMARY OF THE INVENTION

The object of this invention is to provide an artificial knee joint that can support a residual thigh of a prosthesis wearer effectively on a prosthetic lower leg even when the prosthesis wearer walks on an inclined ground surface.

According to this invention, an artificial knee joint includes an upper seat, a lower seat adapted to be connected fixedly to a prosthetic lower leg, and a driving device. The upper seat includes a seat body connected to the lower seat by the driving device, and a movable member connected pivotally to the seat body and adapted to be connected fixedly to a residual thigh. The driving device includes a rotating shaft journalled within the seat body. When a downward force and an upward force are applied respectively to the movable member and the seat body, a gripping member presses against the rotating shaft so as to prevent rotation of the rotating shaft and thus relative movement of the lower seat and the seat body of the upper seat.

As such, when the prosthesis wearer walks on an inclined ground surface, the prosthetic lower leg can support the residual thigh effectively.

BRIEF DESCRIPTION OF THE DRAWINGS

These and other features and advantages of this invention will become apparent in the following detailed description of the preferred embodiments of this invention, with reference to the accompanying drawings, in which.

DETAILED DESCRIPTION OF THE PREFERRED EMBODIMENTS

Before the present invention is described in greater detail in connection with the preferred embodiments, it should be noted that similar elements and structures are designated by like reference numerals throughout the entire disclosure.

Figure 4:
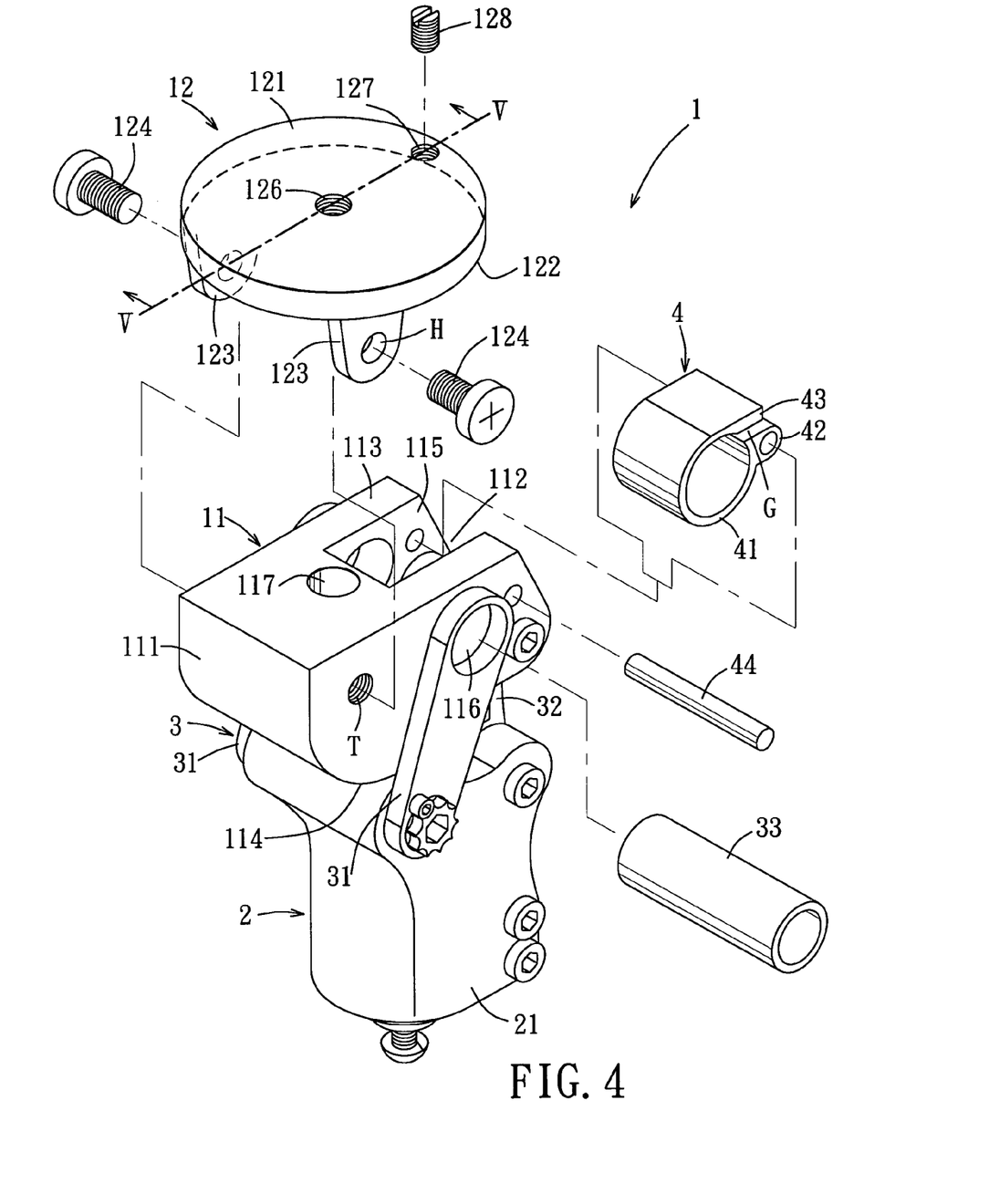
FIG. 4 is an exploded perspective view of the first preferred embodiment of an artificial knee joint according to this invention.
Figure 5:
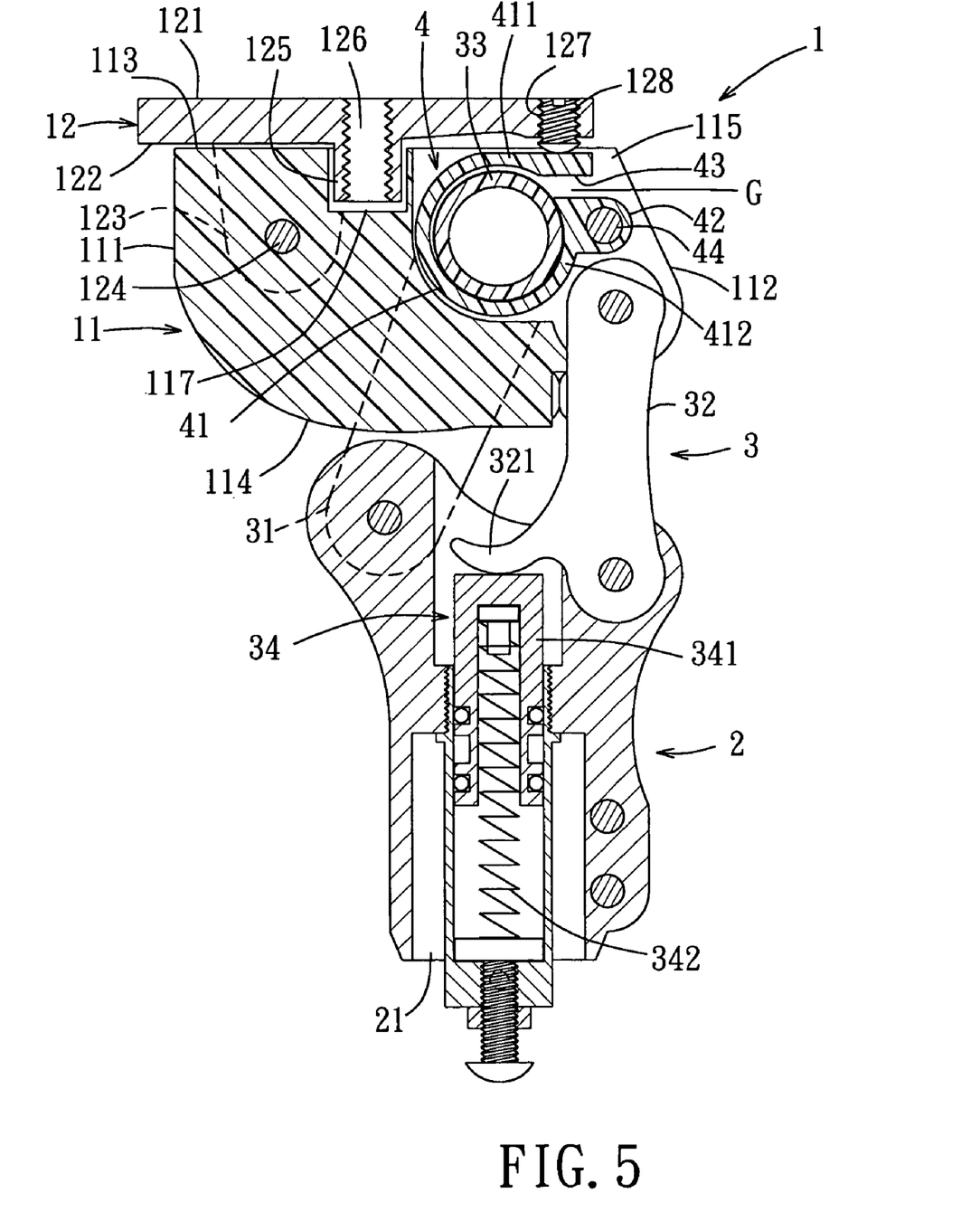
FIG. 5 is a sectional view of the first preferred embodiment, taken along Line V—V in FIG. 4.

Referring to FIGS. 4 and 5, the first preferred embodiment of an artificial knee joint according to this invention is shown to include an upper seat 1, a lower seat 2, a driving device 3 interconnecting the upper and lower seats 1, 2, and a gripping member 4.

The upper seat 1 includes a seat body 11 and a movable member 12.

The seat body 11 has a front end 111, a rear end 112, a top surface 113, a bottom surface 114, a notch 115 formed in a rear end of the top surface 113, a pair of aligned shaft holes 116 (only one is shown in FIG. 4) communicated with the notch 115, and a circular hole 117 formed in the top-surface 113 and disposed in front of the notch 115.

The movable member 12 is disposed above the seat body 11, is shaped as a disk, and has a top surface 121 and a bottom surface 122 that is formed with two downwardly extending lugs 123. Two bolts 124 extend respectively through holes (H) in the lugs 123, and engage respectively threaded holes (T) in the seat body 11 so as to permit rotation of the movable member 12 relative to the seat body 11 about the bolts 124. A cylindrical projection 125 extends integrally from the center of the bottom surface 122, and extends into the circular hole 117 in the seat body 11. A clearance is formed between the projection 125 and the wall of the seat body 11 defining the circular hole 117 so as to permit rotation of the movable member 12 relative to the seat body 11. A front threaded hole 126 is formed through the center of the movable member 12 and the projection 125 so that the movable member 12 can be connected threadedly to a sleeve (not shown) that is disposed fixedly around a residual thigh (not shown). A rear threaded hole 127 is formed through a rear end of the movable member 12. An adjustment bolt 128 engages the rear threaded hole 127, and extends from the bottom surface 122.

The lower seat 2 is disposed under the upper seat 1, and includes a sleeve portion 21 that is disposed fixedly around a prosthetic lower leg (not shown).

The driving device 3 includes two aligned front links 31, a rear link 32, a rotating shaft 33, and a biasing unit 34. The rotating shaft 33 extends through the shaft holes 116 in the seat body 11. The front links 31 have upper ends sleeved respectively and fixedly on two ends of the rotating shaft 33, and lower ends connected pivotally to the lower seat 2. The rear link 32 is disposed behind the front links 31, and has an upper end connected pivotally to the seat body 11 of the upper seat 1, and a lower end connected pivotally to the lower seat 2. The biasing unit 34 includes a cap element 341 that is biased by a spring 342 to press against an integral arm 321 of the rear link 32 in a known manner so as to bias the lower seat 2 to turn relative to the seat body 11 of the upper seat 1 to a predetermined position shown in FIG. 5 and so as to retard rotation of the lower seat 2 away from the predetermined position during walking of the prosthesis wearer. Alternatively, the biasing unit 34 can be designed as a hydraulic cylinder unit.

Because the specific structure of the biasing unit 34 is known in the art and is not pertinent to the claimed invention, a detailed description thereof will be omitted herein for the sake of brevity.

The gripping member 4 is disposed within the notch 115 in the seat body 11 of the upper seat 1, and includes a gripping portion 41, a mounting portion 42, and a suspended plate portion 43. The gripping portion 41 has a C-shaped cross-section, and first and second ends 411, 412 spaced apart from each other to define a gap (G) therebetween, and is sleeved around the rotating shaft 33. The mounting portion 42 is formed integrally with the second end 412 of the gripping portion 41, and is mounted rotatably within the seat body 11 of the upper seat 1 by a pivot pin 44. The suspended plate portion 43 is formed integrally with the first end 411 of the gripping portion 41. The adjustment bolt 128 serves as a pressing portion of the movable member 12, and is rotatable synchronously with the movable member 12 relative to the seat body 11 between a non-pressing position shown in FIG. 6 and a pressing position shown in FIG. 7.

Figure 6:
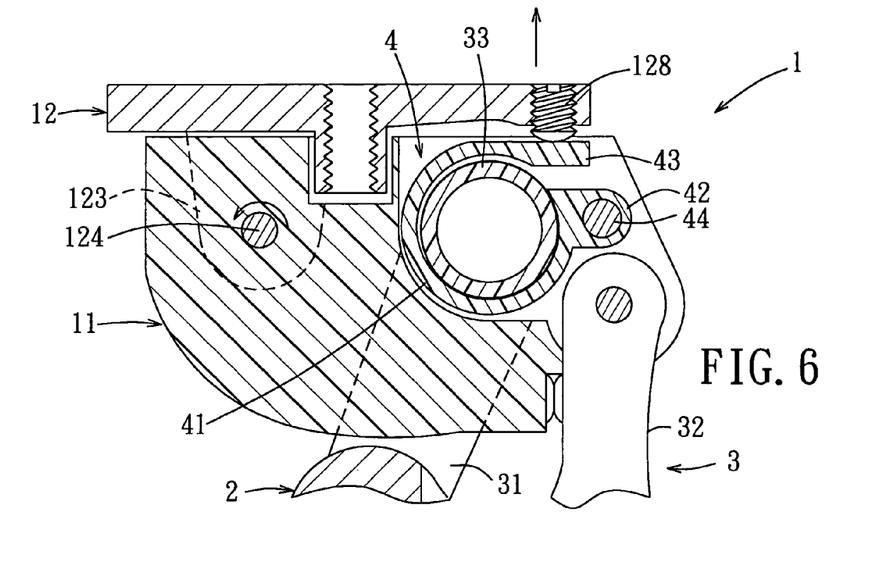
FIG. 6 is a fragmentary sectional view of the first preferred embodiment, illustrating how a pressing portion of a movable member is turned away from a gripping member so as to permit relative movement of a lower seat and a seat body of an upper seat.

Referring to FIG. 6, when the residual thigh is raised to separate the prosthetic lower leg from the ground surface, due to the gravity of an assembly of the seat body 11, the lower seat 2, and the prosthetic lower leg, the free end (i.e. rear end) of the movable member 12 is turned upwardly away from the free end (i.e. rear end 112) of the seat body 11 so that the suspended plate portion 43 of the gripping member 4 is released from the adjustment bolt 128. As such, the gripping portion 41 is sleeved around the rotating shaft 33 in a loose fit manner so that the rotating shaft 33 can rotate within the seat body 11, thereby permitting relative movement of the seat body 11 and the lower seat 2.

Figure 7:
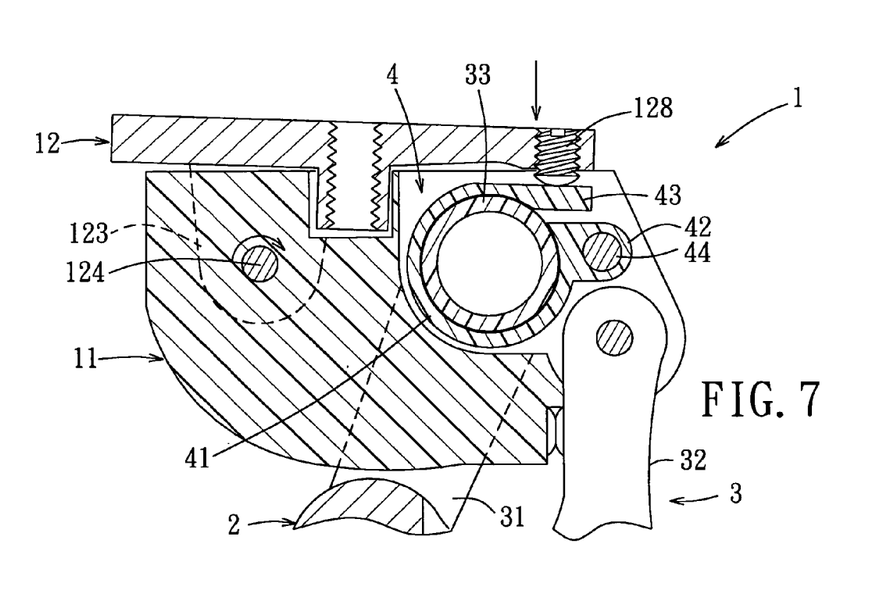
FIG. 7 is a fragmentary sectional view of the first preferred embodiment, illustrating how the pressing portion of the movable member is pressed against the gripping member so as to prevent relative movement of the lower seat and the seat body of the upper seat.

Referring to FIG. 7, when the prosthesis wearer stands on a planar or inclined ground surface, weight of an upper portion of the body of the prosthesis wearer is applied to the movable member 12, and a reactive force is applied from the ground surface to the seat body 11. As such, the rear end of the movable member 12 turns downwardly toward the rear end 112 of the seat body 11 so that the adjustment bolt 128 pushes and moves the suspended plate portion 43 toward the mounting portion 42 to engage the gripping portion 41 with the rotating shaft 33 in a close fit manner, thereby preventing rotation of the rotating shaft 33 within the seat body 11 and thus relative rotation of the residual thigh and the prosthetic lower leg even when the artificial knee joint is flexed. Therefore, the object of this invention can be achieved.

Figure 8:
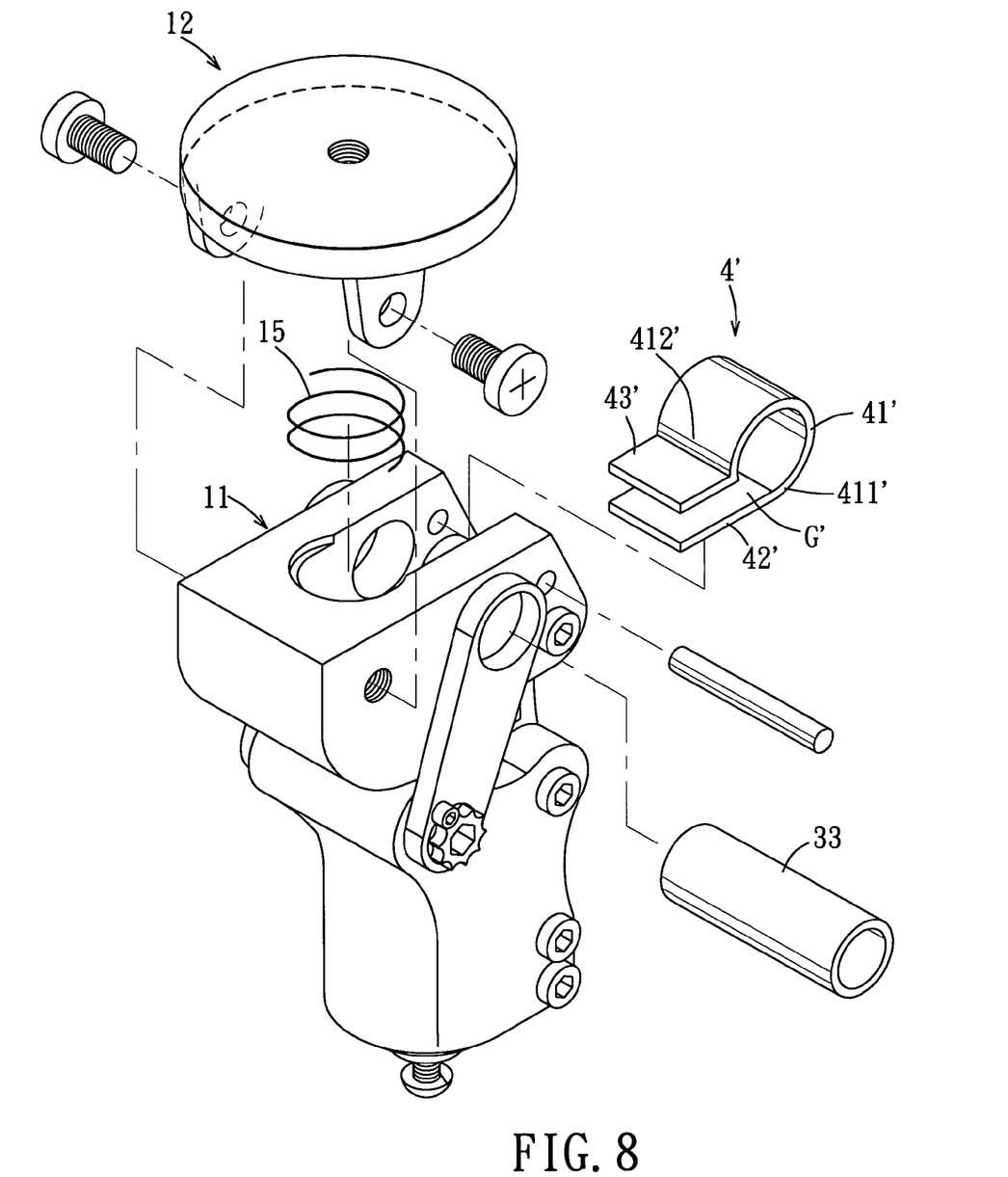
FIG. 8 is a partly exploded perspective view of the second preferred embodiment of an artificial knee joint according to this invention.
Figure 9:
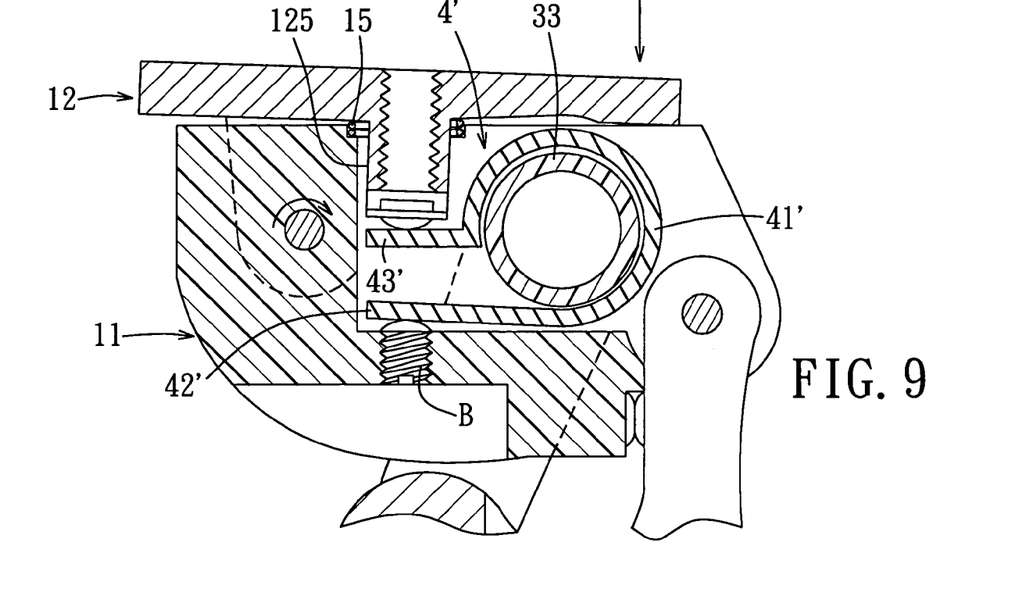
FIG. 9 is a fragmentary sectional view of the second preferred embodiment.

FIGS. 8 and 9 show the second preferred embodiment of an artificial knee joint according to this invention. Unlike the first preferred embodiment, the gripping member 4' includes a gripping portion 41', a fixed plate portion 42', and a suspended plate portion 43'. The gripping portion 41' has a C-shaped cross-section, and first and second ends 411', 412' spaced apart from each other to define a gap (G') therebetween, and is sleeved around the rotating shaft 33 in a loose fit manner. The fixed plate portion 42' is formed integrally with the first end 411' of the gripping portion 41'. The suspended plate portion 43' is formed integrally with the second end 412' of the gripping portion 41'. The seat body 11 is provided with an adjustment bolt (B), against which the fixed plate portion 42' abuts. The cylindrical projection 125 of the movable member 12 abuts against the suspended plate portion 43'. A coiled compression spring 15 is disposed between the seat body 11 and the movable member 12 so as to bias the free end of the movable member 12 to turn away from the rear end of the seat body 11. When the prosthesis wearer stands on the ground, the free end of the movable member 12 turns downwardly relative to the seat body 11 so that the projection 125 of the movable member 12 presses and moves the suspended plate portion 43' toward the fixed plate portion 42'. As such, the gripping portion 41' is sleeved around the rotating shaft 33 in a close fit manner, thereby preventing rotation of the rotating shaft 33 within the seat body 11.

Figure 10:
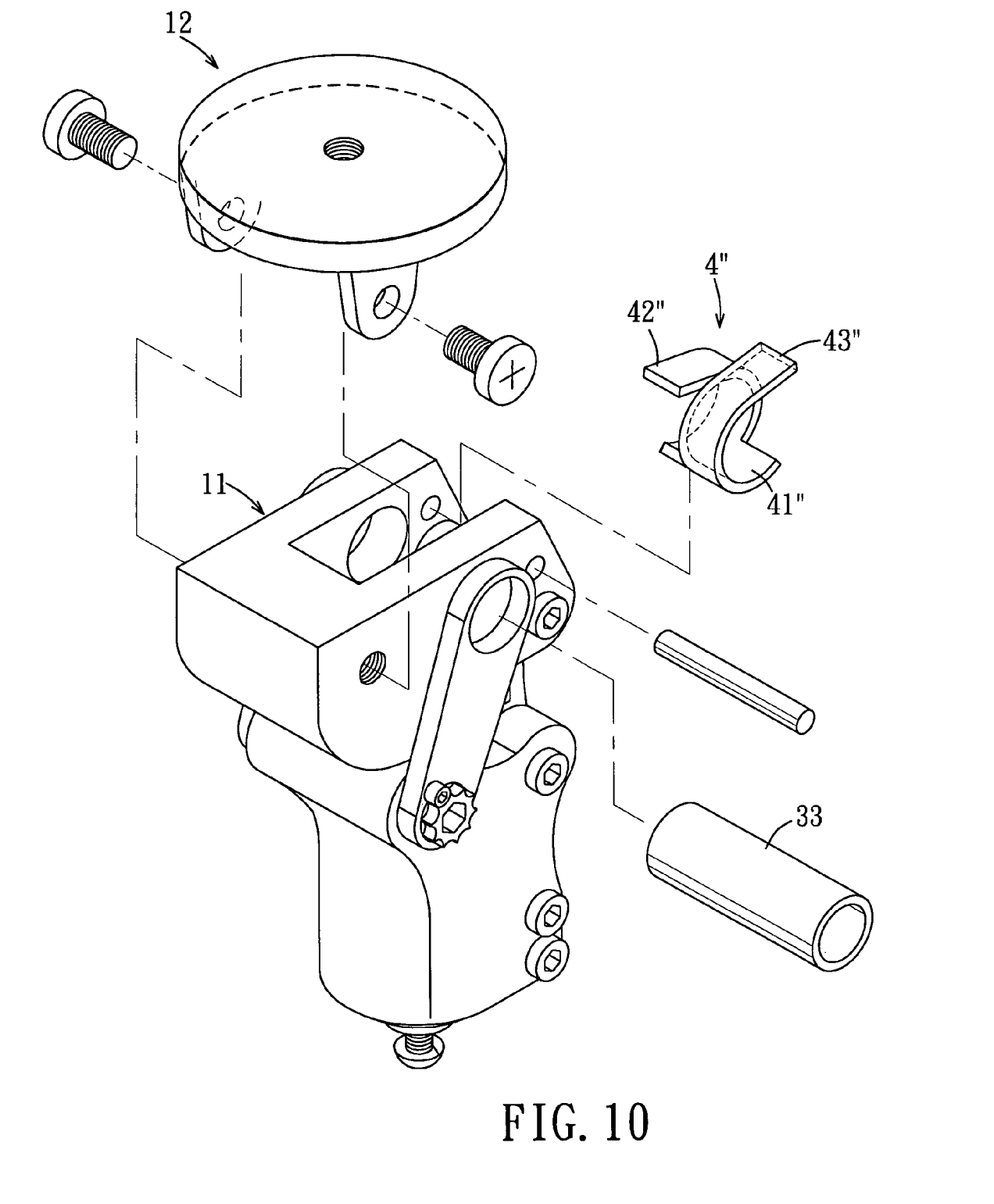
FIG. 10 is a partly exploded perspective view of the third preferred embodiment of an artificial knee joint according to this invention.
Figure 11:
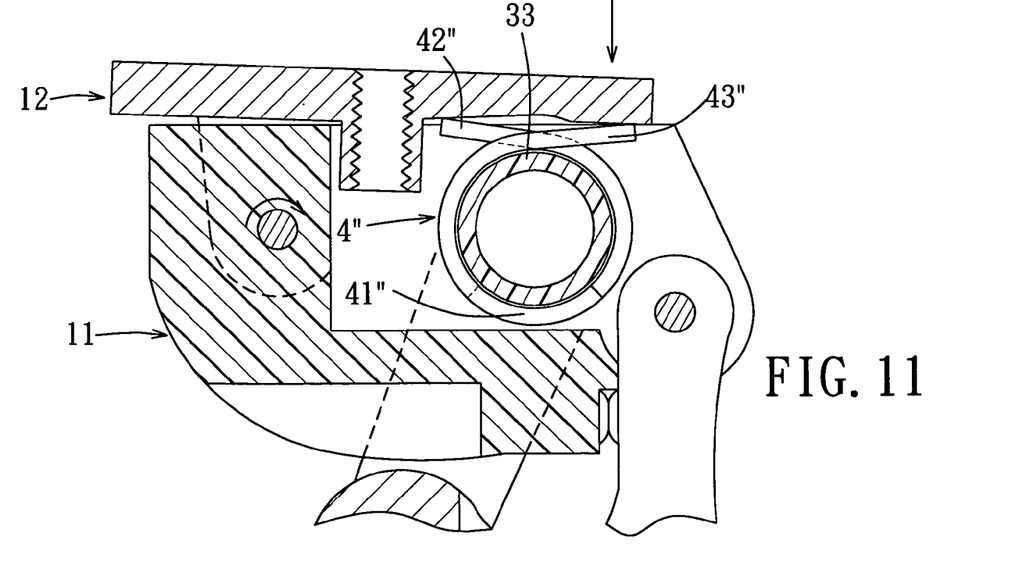
FIG. 11 is a fragmentary sectional view of the third preferred embodiment.

FIGS. 10 and 11 show the third preferred embodiment of an artificial knee joint according to this invention. Unlike the first preferred embodiment, the gripping member 4" includes a base portion 41", a curved first plate portion 42", and a curved second plate portion 43". The first and second plate portions 42", 43" extend respectively and integrally from two opposite sides of the base portion 41" so as to confine the rotating shaft 33 among the base portion 41", the first plate portion 42", and the second plate portion 43". As such, the gripping member 4" is sleeved around the rotating shaft 33 in a loose fit manner. The free end of the movable member 12 abuts against upper ends of the first and second plate portions 42", 43". When the free end of the movable member 12 turns downwardly relative to the seat body 11, it presses the first and second plate portions 42", 43" against the rotating shaft 33 so as to engage the gripping member 4" with the rotating shaft 33 in a close fit manner, thereby preventing rotation of the rotating shaft 33 within the seat body 11.

With this invention thus explained, it is apparent that numerous modifications and variations can be made without departing from the scope and spirit of this invention. It is therefore intended that this invention be limited only as indicated by the appended claims.

We claim:

1. An artificial knee joint for connecting a residual thigh of a prosthesis wearer to a prosthetic lower leg, said artificial knee joint comprising:

an upper seat, including a seat body, and a movable member connected pivotally to said seat body and adapted to be connected fixedly to the residual thigh, said seat body and said movable member respectively having free ends that are rotatable toward and away from each other;

a lower seat disposed under said upper seat and adapted to be connected fixedly to the prosthetic lower leg;

a driving device, connecting said seat body of said upper seat to said lower seat and including a rotating shaft journalled within said seat body of said upper seat, wherein said driving device comprises:

(A) two aligned front links having upper ends connected respectively and fixedly to two ends of said rotating shaft, and lower ends connected pivotally to said lower seat;

(B) a rear link disposed behind said front links and having an upper end connected pivotally to said seat body of said upper seat, and a lower end connected pivotally to said lower seat; and (C) a biasing unit disposed within said lower seat and connected to said rear link so as to bias said lower seat to turn relative to said seat body of said upper seat to a predetermined position, so as to retard rotation of said lower seat away from said predetermined position during walking of the prosthesis wearer; and a gripping member disposed movably on said seat body of said upper seat and movable, when a downward force and an upward force are applied respectively to said movable member and said seat body of said upper seat to turn said free ends of said seat body and said movable member of said upper seat toward each other, to press against said rotating shaft so as to prevent rotation of said rotating shaft within said seat body of said upper seat and thus relative movement of said lower seat and said seat body of said upper seat.

2. The artificial knee joint as claimed in claim 1, wherein said gripping member includes a gripping portion that has a C-shaped cross-section, and first and second ends spaced apart from each other to define a gap therebetween, and that is sleeved around said rotating shaft in a loose fit manner, a mounting portion that is formed integrally with said second end of said gripping portion and that is mounted pivotally within said seat body of said upper seat, and a suspended plate portion that is formed integrally with said first end of said gripping portion, said movable member being formed with a fixed pressing portion that is rotatable relative to said seat body of said upper seat to move said suspended plate portion of said gripping member toward said mounting portion of said gripping member when the downward force and the upward force are applied respectively to said movable member and said seat body of said upper seat to turn said free ends of said seat body and said movable member of said upper seat toward each other, such that said gripping portion of said gripping member is sleeved around said rotating shaft in a close fit manner, thereby preventing rotation of said rotating shaft within said seat body of said upper seat.

3. The artificial knee joint as claimed in claim 1, wherein said gripping member includes a gripping portion, a fixed plate portion, and a suspended plate portion, said gripping portion having a C-shaped cross-section, and first and second ends spaced apart from each other to define a gap therebetween, and being sleeved around said rotating shaft in a loose fit manner, said fixed plate portion being formed integrally with said first end of said gripping portion, said suspended plate portion being formed integrally with said second end of said gripping portion, said seat body being provided with an adjustment bolt, against which said fixed plate portion abuts, said artificial knee joint further including a coiled compression spring that is disposed between said seat body and said movable member so as to bias said free ends of said seat body and said movable member to turn away from each other, said movable member being formed with a projection that is rotatable relative to said seat body of said upper seat to move said suspended plate portion of said gripping member toward said fixed plate portion of said gripping member when the downward force and the upward force are applied respectively to said movable member and said seat body of said upper seat to turn said free ends of said seat body and said movable member of said upper seat toward each other, such that said gripping portion of said gripping member is sleeved around said rotating shaft in a close fit manner, thereby preventing rotation of said rotating shaft within said seat body of said upper seat.

4. The artificial knee joint as claimed in claim 1, wherein said gripping member includes a base portion, a curved first plate portion, and a curved second plate portion, said first and second plate portions extending respectively and integrally from two opposite sides of said base portion so as to confine said rotating shaft among said base portion, said first plate portion, and said second plate portion, said gripping member being sleeved around said rotating shaft in a loose fit manner, said free end of said movable member abutting against said first and second plate portions, said free end of said movable member turning downwardly relative to said seat body of said upper seat when the downward force and the upward force are applied respectively to said movable member and said seat body of said upper seat to turn said free ends of said seat body and said movable member of said upper seat toward each other, such that said gripping member is sleeved around said rotating shaft in a close fit manner, thereby preventing rotation of said rotating shaft within said seat body of said upper seat.

* * * * *